United States Patent
Roetzer

(12) 
(10) Patent No.: US 6,752,630 B2
(45) Date of Patent: Jun. 22, 2004

(54) DENTAL RETRACTOR AND FLUID CONTROL SYSTEM

(76) Inventor: Patrick L. Roetzer, 142 E. D St., Benicia, CA (US) 94510

( * ) Notice: Subject to any disclaimer, the term of this patent is extended or adjusted under 35 U.S.C. 154(b) by 0 days.

(21) Appl. No.: 10/120,318

(22) Filed: Apr. 9, 2002

(65) Prior Publication Data

US 2004/0091835 A1 May 13, 2004

(51) Int. Cl.[7] .................................................. A61C 5/00
(52) U.S. Cl. ....................................... 433/140; 600/242
(58) Field of Search ................................. 433/136, 140; 600/242

(56) References Cited

U.S. PATENT DOCUMENTS

| | | | | |
|---|---|---|---|---|
| 776,302 A | * | 11/1904 | Crockett | .................... 600/242 |
| 1,389,436 A | * | 8/1921 | Cameron | .................... 600/219 |
| 3,234,942 A | | 2/1966 | Simor | .......................... 604/20 |
| 3,690,004 A | * | 9/1972 | Frush | ............................ 433/37 |
| 4,053,984 A | * | 10/1977 | Moss | .......................... 433/140 |
| 5,730,597 A | * | 3/1998 | Luttrell | ....................... 433/140 |
| 6,206,692 B1 | * | 3/2001 | Komiyama | .................. 433/37 |

* cited by examiner

Primary Examiner—John J. Wilson
(74) Attorney, Agent, or Firm—Theodore J. Bielen, Jr.

(57) ABSTRACT

A dental retractor system used to manipulate positioning of the cheeks and to control saliva flow. The system includes a handle connected to first and second legs that are extended from the handle in a fork or horseshoe configuration. A pair of flaps distend from the legs and are angularly arranged to lie adjacent inner cheeks of the patient with or without interaction with a dry angle.

10 Claims, 2 Drawing Sheets

DENTAL RETRACTOR AND FLUID CONTROL SYSTEM

BACKGROUND OF THE INVENTION

The present invention relates to a novel and useful dental retractor system.

Retractors have been employed in the past to position the cheeks of a dental patient during dental procedures such as the repair of teeth and gums, obtaining of a dental impressions, and the like. Such procedures also entail the rapid generation of saliva by the patient from salivary glands such as the parotid gland, sublingual gland, submandibular gland and auxiliary salivary glands found within the mouth of a patient. Since many dental procedures require a dry environment, thus, it is important to control the saliva secretion during dental procedures such as the application of sealants on tooth surfaces.

In the past, absorbent materials such as paper, cotton, and the like have been placed in the mouth to control positioning of the lips and cheeks and saliva flow. Suction devices have also been used to move fluids from the mouth during dental procedures. Unfortunately, such prior art devices interfere with the practitioner's dental work.

Reference is made to U.S. Pat. No. 3,234,942 which shows a tray for the application of fluoride to patient's teeth. However, the tray arrangement of this patent does not describe salivary gland control.

A dental retractor system which positions the lips and cheeks of a patient, as well as controlling saliva production would be a notable advance in the dental arts.

BRIEF SUMMARY OF THE INVENTION

In accordance with the present invention a novel and useful dental retractor system is herein provided.

The system of the present invention uses a handle which is easily grasped by the dental practitioner. Connected to the handle are a pair of legs which extend outwardly and flex to allow easy insertion and removal from the mouth of a patient. In this regard the retractor system of the present invention is removable from a patient's mouth using a straight horizontal pulling force. This horizontal path of motion obviates interference with dental impression trays and other dental implements found in the mouth of the patient. First and second legs are formed into a U-shaped or horseshoe shaped member, in this regard.

First and second flaps are connected to the first and second legs which extend outwardly from the handle, respectively. Each flap is connected to and angularly extended from a leg and is sized to lie adjacent the inner cheek of the patient when placed within the mouth of the patient. Each flap is generally positioned opposite the parotid or Stensen's duct, the main conduit for saliva produced by the parotid gland. The flaps may be used in conjunction with other dental devices such as dry angles to stabilize the same and to avoid interference with dental procedures.

In addition, the intermediate portion between the first and second legs includes a surface which is capable of supporting absorbent material, such as cotton rolls, which are capable of absorbing saliva produced by the auxiliary salivary glands generally found the between the lips and the teeth of the patient.

Insertion of the dental retractor system into the mouth of the patient permits the practitioner to perform multiple dental procedures such as obtaining of dental impressions, insertion of orthodontic brackets, oral surgery, and bonding and sealing procedures, which normally require a dry environment. In addition, the retractor is capable of protecting the patient from drilling procedures and exposure to finely divided material which are produced by the same.

It may be apparent that a novel and useful dental retractor system has been hereinabove described.

It is therefore an object of the present invention to provide a dental retractor system which is capable of positioning the lips and cheeks of a patient and controlling saliva flow during dental procedures.

Another object of the present invention is to provide a dental retractor system which is especially useful in the application of dental sealants by a dental practitioner.

A further object of the present invention is to provide a dental retractor system which achieves lip and cheek retraction to protect the same against mechanical trauma due to rotary cutting instruments employed by a dental practitioner.

Another object of the present invention is to provide a dental retractor system which protects against over spray and ricochet spray during dental material removal processes.

Yet another object of the present invention is to provide a dental retractor system which is particularly useful during oral surgery procedures to protect the inner cheek from damage which may be inflicted by the oral surgery instruments.

Another object of the present invention is to provide a dental retractor system which is easily removed from the patient's mouth along a horizontal path.

Yet another object of the present invention is to provide a dental retractor system which controls the positioning of a dry angle and keeps the dry angle from interfering with dental procedures.

The invention possesses other objects and advantages especially as concerns particular characteristics and features thereof which will become apparent as the specification continues.

Figure 1:
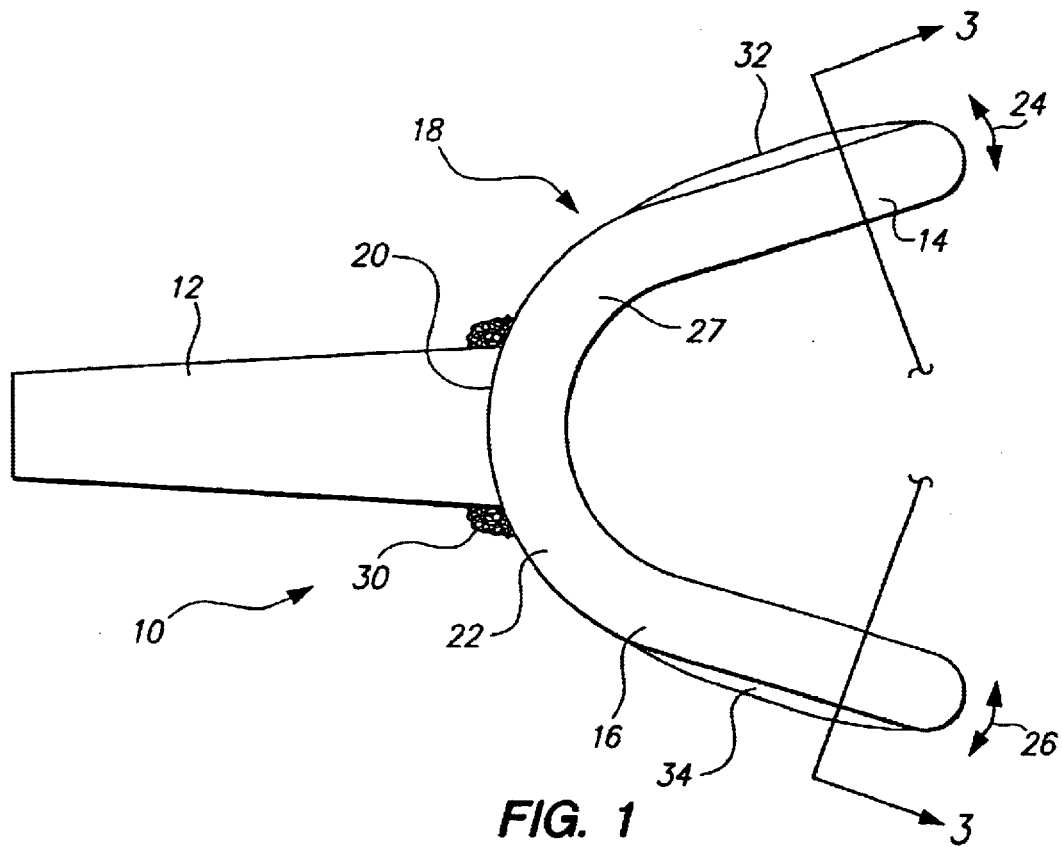
FIG. 1 is a top plan view of the retractor system of the present invention for lower jaw usage, or a bottom plan view of the retractor system of the present invention for upper jaw usage.

For a better understanding of the invention reference is made to the following detailed description of the preferred embodiments thereof which should be taken in conjunction with the prior described drawings.

DETAILED DESCRIPTION OF THE PREFERRED EMBODIMENTS OF THE INVENTION

Various aspects of the present invention will evolve from the following detailed description of the preferred embodiments thereof which should be taken together with the prior delineated drawings.

The preferred embodiment of the present invention is noted in the drawings by reference character 10. Retractor system 10 includes as one of its elements a handle 12 which is easily grasped by the dental practitioner when retractor system 10 is in use. Handle 12 may be formed of any rigid or semi rigid material, and is preferably compatible for oral tissue during dental procedures.

System 10 also includes legs 14 and 16. Legs 14 and 16 are formed from a U-shaped member 18 which is connected to handle 12 along surface 20. Intermediate portion 22 of unit 18 also terminates in legs 14 and 16. Slightly convex surface 27 spans legs 14 and 16. Directional arrows 24 and 26 show the flexibility or springiness attributed to legs 14 and 16. Again, unit 18, including legs 14 and 16, may be formed of a similar material to handle 12 such as plastic, and the like.

Slightly convex surface 28 of unit 18 is capable of supporting an absorbent material 30 at intermediate portion 22 thereof. Absorbent material 30 is intended to absorb the flow of saliva within the mouth of the user, which will be described in greater detail hereinafter.

Figure 2:
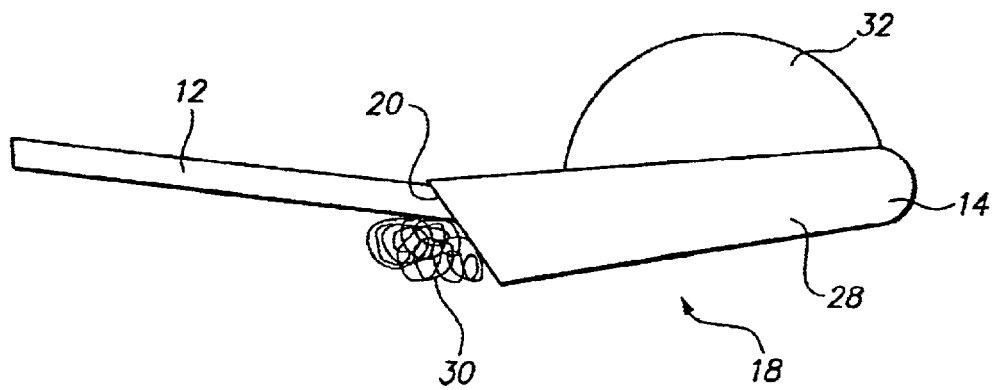
FIG. 2 is a right side view of the retractor system of the present invention, in position for use on a lower jaw.

Flaps 32 and 34, FIGS. 1 and 2, angularly and rigidly connect to legs 14 and 16, respectively. Flaps 32 and 34 are constructed of the same material as legs 14 and 16 and extend from legs 14 and 16, respectively. Again, flaps 34 and 36, in combination with dry angles 48 and 50, FIG. 3, are used to control the flow of fluid or saliva within the mouth of the user.

Figure 3:
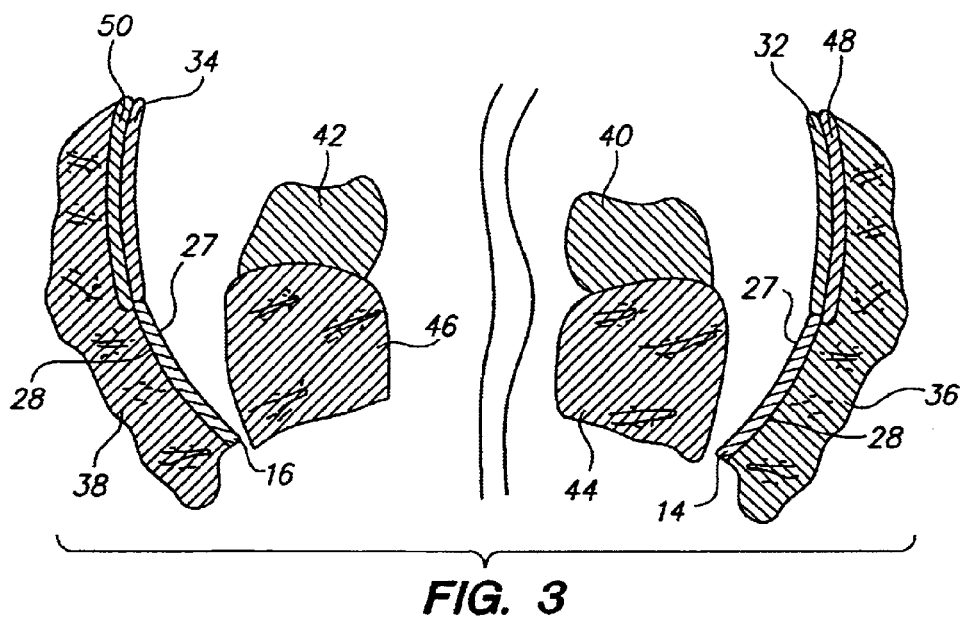
FIG. 3 is a sectional view taken along line 3—3 of FIG. 1.
Figure 4:
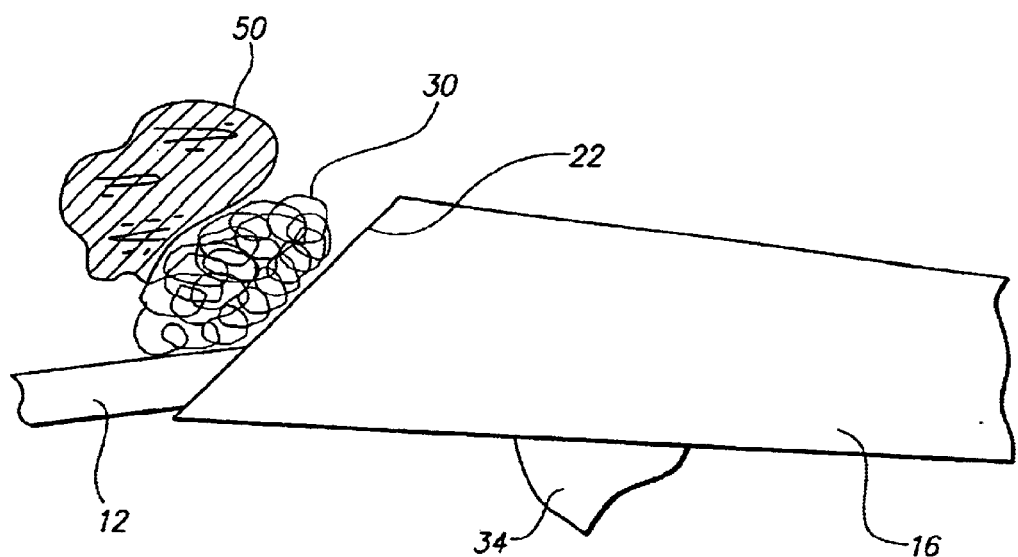
FIG. 4 is a side elevational view of the retractor system of the present invention in place against an auxiliary salivary duct adjacent the upper lip of a patient.

In operation, with reference to FIG. 3, it may be observed that retractor system 10 has been placed within the mouth at the lower jaw of a patient. In this regard, legs 14 and 16 lie adjacent inner cheeks 36 and 38. Teeth 40 and 42 lie on the other side of legs 14 and 16, respectively. Teeth 40 and 42 extend from gums 44 and 46, respectively. Dry angles 48 and 50 lie against cheeks 36 and 38, respectively and are held firmly in place by flaps 32 and 34, respectively. Dry angles 48 and 50 are intended to shield the flow of saliva from the parotid gland and duct which is usually shown in the region found in FIG. 3. Thus, saliva is prevented from flowing to the vicinity of teeth 40 and 42 which may be important when sealants are employed requiring a dry environment. FIG. 4 depicts the use of system 10, inverted from FIG. 3 in which absorbent material 30 on surface 28 at intermediate portion 22 presses against an upper lip 52 adjacent the teeth (not shown) of the patient. Such positioning absorbs the flow of saliva from auxiliary saliva glands found in that area of the mouth of the patient, i.e. the inner mucosa of the lips of the patient mouth. Thus, the combination of flaps 32 and 34, as well as absorbent material 30 on surface 28 greatly controls the flow of fluid such as saliva in the mouth of the user when retractor system 10 is used with respect to the upper or lower jaw of a patient. After dental procedures have been completed retractor system 10 is removed by pulling handle outwardly in a straight and horizontal path. Springy legs 14 and 16 do not interfere with the commissure of the patient's lips during this maneuver.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental retractor system for use in the mouth of a patient adjacent the inner cheeks, comprising:

a. a handle;

b. first and second legs connected to said handle, said first and second legs each extending outwardly from said handle a certain distance of projection and being separated from one another;

c. a first flap connected to said first leg and extending outwardly therefrom only along said certain distance of projection of said first leg from said handle;

d. a second flap connected to said second leg and extending outwardly therefrom only along said certain distance of projection of said first leg from said handle, said first and second legs with said connected first and second flaps being sized to enter the mouth of a patient and lie adjacent the inner cheeks in the immediate vicinity of a parotid gland and duct; and e. means for resiliently attaching said first and second legs to said handle.

2. The system of claim 1, in which said first and second legs are formed of a flattened material.

3. The system of claim 2 in which said first and second flaps are formed of flattened material and are angularly connected to said first and second legs, respectively.

4. The system of claim 3 which further comprises means for rigidly connecting said first and second flaps to said first and second legs, respectively.

5. The system of claim 1 in which said first and second legs form a U-shaped member of continuous configuration.

6. The system of claim 1 used with an absorbent material and which additionally comprises an intermediate portion between said first and second legs, said intermediate portion including a surface capable of supporting the absorbent material.

7. The system of claim 6 in which said first and second legs are formed of a flattened material.

8. The system of claim 6 in which said first and second flaps are formed of flattened material and are angularly connected to said first and second legs, respectively.

9. The system of claim 8 which further comprises means for rigidly connecting said first and second flaps to said first and second legs, respectively.

10. The system of claim 6 in which said first and second legs form a U-shaped member of continuous configuration.

* * * * *